US011511254B2

(12) United States Patent
Feyeux et al.

(10) Patent No.: US 11,511,254 B2
(45) Date of Patent: Nov. 29, 2022

(54) PROCESS FOR PRODUCING CAPSULES MADE OF AN EXTERNAL SHELL OF CROSSLINKED HYDROGEL SURROUNDING A CENTRAL CORE

(71) Applicants: UNIVERSITE DE BORDEAUX, Bordeaux (FR); CENTRE NATIONAL DE LA RECHERCHE SCIENTIFIQUE, Paris (FR); INSTITUT D'OPTIQUE THÉORIQUE ET APPLIQUÉE, Palaiseau (FR)

(72) Inventors: Maxime Feyeux, Talence (FR); Kevin Alessandri, Bordeaux (FR); Pierre Nassoy, Bordeaux (FR)

(73) Assignees: UNIVERSITE DE BORDEAUX, Bordeaux (FR); CENTRE NATIONAL DE LA RECHERCHE SCIENTIFIQUE, Paris (FR); INSTITUT D'OBTIQUE THÉORIQUE ET APPLIQUÉE, Palaiseau (FR)

( * ) Notice: Subject to any disclaimer, the term of this patent is extended or adjusted under 35 U.S.C. 154(b) by 184 days.

(21) Appl. No.: 16/765,964

(22) PCT Filed: Nov. 20, 2018

(86) PCT No.: PCT/EP2018/081913
§ 371 (c)(1),
(2) Date: May 21, 2020

(87) PCT Pub. No.: WO2019/101734
PCT Pub. Date: May 31, 2019

(65) Prior Publication Data
US 2020/0360888 A1  Nov. 19, 2020

(30) Foreign Application Priority Data
Nov. 21, 2017 (FR) .................................... 1761018

(51) Int. Cl.
*B01J 13/16* (2006.01)
*C12N 11/10* (2006.01)

(52) U.S. Cl.
CPC .............. *B01J 13/16* (2013.01); *C12N 11/10* (2013.01)

(58) Field of Classification Search
CPC . B01J 13/16; B01J 13/14; C12N 11/10; A23P 30/25; A23P 10/30; A61K 2800/10; A61K 2800/412; A61K 2800/621; A61K 2800/652; A61K 8/042; A61K 8/11; A61K 8/20; A61K 9/5036; A61K 2035/128; A61Q 19/00
See application file for complete search history.

(56) References Cited

U.S. PATENT DOCUMENTS

| 6,377,387 B1 | 4/2002 | Duthaler et al. |
| 2005/0158395 A1 | 7/2005 | Zimmermann et al. |
| 2011/0008293 A1 | 1/2011 | Bhandari |
| 2013/0078308 A1 | 3/2013 | Hashimoto et al. |
| 2015/0017676 A1* | 1/2015 | Bibette ............... B01J 13/08 435/174 |

FOREIGN PATENT DOCUMENTS

JP   S63-236534   10/1988

OTHER PUBLICATIONS

Batubara, I. et al. "Leydig Cells Encapsulation with Alginate-Chitosan: Optimization of Microcapsule Formation" *Journal of Encapsulation and Adsorption Sciences*, 2012, pp. 15-20, vol. 2.
Written Opinion in International Application No. PCT/EP2018/081913, dated Dec. 10, 2018, pp. 1-11.

* cited by examiner

*Primary Examiner* — Irina S Zemel
(74) *Attorney, Agent, or Firm* — Greer, Burns & Crain, Ltd.

(57) ABSTRACT

The invention relates to a process for producing a plurality of capsules, each comprising an external shell of crosslinked hydrogel surrounding a central core, according to which a hydrogel solution and a composition of interest, intended to form the central core, are concentrically co-extruded so as to form mixed drops, each comprising a layer of hydrogel solution surrounding a drop of liquid composition of interest, characterized in that the co-extrusion step is carried out above a crosslinking aerosol so that the mixed drops pass through said crosslinking aerosol, such that the layer of hydrogel solution at least partially crosslinks around the drop of liquid composition of interest on contact with said aerosol.

10 Claims, No Drawings

PROCESS FOR PRODUCING CAPSULES MADE OF AN EXTERNAL SHELL OF CROSSLINKED HYDROGEL SURROUNDING A CENTRAL CORE

CROSS-REFERENCE TO RELATED APPLICATION

This application is the U.S. national stage application of International Patent Application No. PCT/EP2018/081913, filed Nov. 20, 2018.

The present invention relates to a process for the manufacture of capsules formed of an outer shell of crosslinked hydrogel surrounding a central core which may be liquid. More specifically, the invention relates to a manufacturing process for encapsulating a composition of interest to form capsules in which the properties of said composition of interest are preserved.

Encapsulation processes have been developed in recent years to produce capsules consisting of an outer shell containing a central composition, usually liquid. Such capsules are used in particular in the pharmaceuticals and cosmetics fields. The central composition contains an active agent protected from external damage and whose release can be better controlled.

Generally, capsules are obtained by concentrically coextruding a hydrogel solution, intended after crosslinking to form the outer shell, with a composition of interest to be encapsulated. At the exit of the extruder, mixed drops are obtained, composed of a layer of hydrogel solution surrounding a drop of the composition of interest. The mixed drops then fall into a bath comprising crosslinking agents, in which crosslinking of the hydrogel layer takes place.

However, a breaking down of the mixed drops is often observed when they fall from the extruder to the crosslinking bath and/or when the mixed drops impact with the crosslinking bath. The outer layer of hydrogel breaks partially or totally under the force of the impact, resulting in partial mixing of the drop of composition of interest with the liquid layer of hydrogel before crosslinking, or even expulsion of the drop of composition of interest towards the outside of the mixed drop during the crosslinking of the hydrogel. Also, the capsules recovered are not of regular shape or size and/or of controlled topology.

As a result, it is often necessary to add a surfactant to the hydrogel solution to prevent the mixed drops from bursting on impact with the crosslinking bath. Surfactants can come into contact with the contents of the capsule and alter its properties. Thus, when the capsules contain active agents or cells, this can have significant negative consequences, such as reducing the effectiveness of the active agent or leading to cell death. Similarly, when the capsules contain an agrifood composition, the organoleptic properties of that composition may be altered by interaction with the surfactant.

In addition, the concentration of crosslinking agents is necessarily high to freeze the structure of the drop on impact. As a result, the crosslinking agents pass through the layer of hydrogel solution during crosslinking and penetrate inside the capsule. As well as interaction with surfactants, contact of the crosslinking agent with the interior of the capsule can alter the properties of its content.

These crosslinking agents and surfactants can also be irritating to the human body. It is therefore sometimes necessary, depending in particular on the intended use of the capsules, to carry out thorough rinsing steps to remove all traces of crosslinking agent and/or surfactant from the surface and/or within the capsules. These rinsing steps significantly reduce the yield and increase the production cost of such capsules.

Therefore, there is a need for a process for the manufacture of hydrogel capsules containing a composition of interest, in particular a liquid composition, which allows capsules of controlled shape and structure to be obtained, without excessive cost, at high throughput.

SUMMARY OF THE INVENTION

Working on these issues, the inventors discovered that it is possible to at least partially crosslink the hydrogel layer around the drop of composition of interest before the capsules impact the recovery bath in which they are received. Such pre-crosslinking of the hydrogel around the drop of composition of interest prevents the risk of the capsules breaking down. In addition, the risks of contact of the capsule contents with a crosslinking agent and/or a possible surfactant are also reduced. To allow such early crosslinking, the inventors have developed a process in which the mixed drops, conventionally obtained by coextrusion of a hydrogel solution and the composition of interest, pass through an aerosol formed of microparticles (liquid or solid) comprising a crosslinking agent. The microparticles coalesce on the surface of the mixed drops during their fall through said aerosol, and allow at least partial crosslinking of the hydrogel. Advantageously, the outermost layer of the hydrogel is crosslinked, forming a rigid or semi-rigid shell around the drop of composition of interest. Spraying or fogging by jet would, on the contrary, favor the penetration of the microparticles of crosslinking agent into the interior of the mixed drops, thus causing the outer layer of hydrogel to mix with the drop of composition of interest forming the core of the mixed drop, so as to alter the structuring of the mixed drop. Contrary to spraying by jet, the use of a mist, or aerosol, in which the microparticles are suspended in the air, promotes the deposition of a thin layer of crosslinking agent all around the mixed drops, causing at least partial crosslinking of the surface of the hydrogel layer. Such a process advantageously makes it possible to dispense with the use of surfactant, which can be particularly interesting for the production of capsules containing cells. If necessary, if the crosslinking is not sufficient, it is possible to continue it in a crosslinking bath. According to the invention, the precrosslinked layer of hydrogel protects the capsules on impact with the liquid in which they are received after their fall. Furthermore, when these capsules are immersed in a crosslinking bath, the presence of the pre-crosslinked layer, even if very thin, is sufficient to protect the structure of the capsule and prevent its deformation. Furthermore, the immersion times in any crosslinking baths can be reduced and the subsequent rinsing steps can also be reduced.

The invention therefore relates to a process for manufacturing a plurality of capsules each comprising an outer shell of crosslinked hydrogel surrounding a central core, wherein a hydrogel solution and an aqueous composition of interest, designed to form the central core, are concentrically coextruded to form mixed drops each comprising a layer of hydrogel solution surrounding a drop of composition of interest, characterized in that the coextrusion step is carried out above a crosslinking aerosol so that the mixed drops pass through said crosslinking aerosol, so that the layer of hydrogel solution crosslinks at least partially around the drop of composition of interest in contact with said aerosol.

The invention also relates to capsules, obtainable by such a process, in which the outer surface of the hydrogel layer bears the trace of contact with the crosslinking aerosol in the form of surface irregularities caused by impacts. Such capsules are therefore characterized by an outer layer of crosslinked hydrogel surrounding a central core consisting of a drop of composition of interest, wherein the outer surface of the hydrogel layer is honeycombed, i.e. covered with honeycombs.

The invention also relates to capsules as described above, in which the central core comprises cells having an excess mortality caused by encapsulation of less than 20%, preferentially less than 10%.

DETAILED DESCRIPTION

The process according to the invention is characterized by a step of at least partial crosslinking of a hydrogel layer around a central core by means of a crosslinking aerosol, the microparticles of which coalesce on the surface of the hydrogel layer.

Specifically, the mixed drops formed at the extruder outlet are projected by the extrusion flow towards a receiving surface and pass through the aerosol arranged between the extruder outlet and the receiving surface.

Receiving surface means the element on or into which the capsules fall after passing through the crosslinking aerosol. In an embodiment, the receiving surface consists of a recovery bath, optionally including a crosslinking solution.

According to the invention, any extrusion process for concentrically coextruding a hydrogel solution and a composition of interest can be used. In particular, it is possible to make mixed drops by adapting the method and the microfluidic device described in Alessandri et al. (PNAS, Sep. 10, 2013 vol. 110 no. 37 14843-14848; Lab on a Chip, 2016, vol. 16, no. 9, p. 1593-1604) or in Onoe et al., (Nat Material 2013, 12(6):584-90), so that the solutions are coextruded over a crosslinking aerosol. For example, the process according to the invention is carried out by means of an extrusion device with double or triple concentric shells as described in patent FR2986165.

According to the invention, "mixed drops" means the drops obtained at the exit of an extruder by means of which a peripheral hydrogel solution and a composition of central interest have been coextruded in a concentric manner. The mixed drops are thus composed of a layer of non-crosslinked hydrogel solution surrounding a drop of composition of interest. A "drop of composition of interest" is defined as a small volume of the composition of interest, which may be a liquid, solution, colloid, or suspension, such as a gel, cream, etc. In general, the composition of interest is advantageously aqueous. It can thus be an aqueous composition in liquid form, a gel, a cream, etc. In the case of a composition of interest in gel form, said gel is advantageously different from the hydrogel used to form the outer layer of the mixed drops. Preferably, the composition of interest does not include an alginate, and more generally does not include crosslinkable compounds.

Conversely, "capsules" means products derived from mixed drops, after at least partial crosslinking of the hydrogel layer. The capsules are therefore composed of an outer hydrogel shell at least partially stiffened by crosslinking around the drop of composition of interest.

Mixed drops such as capsules are advantageously spherical in shape.

In the context of the invention, "crosslinked hydrogel outer shell" means a three-dimensional structure formed from a matrix of polymer chains swollen by a liquid, and preferably water. Such a crosslinked hydrogel outer shell is obtained by crosslinking a hydrogel solution. Advantageously, the polymer or polymers of the hydrogel solution are polymers which are crosslinkable when subjected to a stimulus, such as temperature, pH, ions, etc. Advantageously, the hydrogel solution used is biocompatible, in the sense that it is not toxic to cells. If the composition of interest to be encapsulated includes cells, the hydrogel layer advantageously allows the diffusion of oxygen and nutrients, as well as carbon dioxide and metabolic waste to feed the cells and allow their survival. The polymers in the hydrogel solution can be of natural or synthetic origin. For example, the hydrogel solution contains one or more polymers among sulfonate-based polymers, such as sodium polystyrene sulfonate, acrylate-based polymers, such as sodium polyacrylate, polyethylene glycol diacrylate, the compound gelatin methacrylate, polysaccharides, including polysaccharides of bacterial origin, such as gellan gum, or of vegetable origin, such as pectin or alginate.

In an embodiment, the hydrogel solution comprises at least alginate. Preferentially, the hydrogel solution comprises only alginate. In the context of the invention, "alginate" means linear polysaccharides formed from β-D-mannuronate (M) and α-L-guluronate (G), salts and derivatives thereof. Advantageously, the alginate is a sodium alginate, composed of more than 80% G and less than 20% M, with an average molecular weight of 100 to 400 kDa (for example: PRONOVA® SLG100) and a total concentration of between 0.5% and 5% by density (weight/volume).

According to the invention, the crosslinking aerosol comprises at least one crosslinking agent adapted to crosslink a hydrogel comprising at least one hydrophilic polymer, such as alginate, when brought into contact therewith. Preferably, the crosslinking aerosol is free of surfactant.

In an embodiment, the crosslinking aerosol is formed from microdroplets of a crosslinking solution. Such an aerosol can be obtained by any means conventionally used to form an aerosol from a liquid solution, in particular a membrane mister. In another embodiment, the crosslinking aerosol is made up of solid microparticles of crosslinking agent, for example in the form of a carbonate and/or calcium chloride micropowder.

The crosslinking solution advantageously contains at least one divalent cation. The crosslinking solution may also be a solution comprising another known crosslinking agent of the alginate or hydrophilic polymer to be crosslinked, or a solvent, for example water or an alcohol, adapted to allow crosslinking by irradiation or by any other technique known in the art. Advantageously, the crosslinking solution is a solution comprising at least one divalent cation. Preferably, the divalent cation is a cation enabling alginate to be crosslinked in solution. It can be, for example, a divalent cation selected from the group comprising $Ca^{2+}$, $Mg^{2+}$, $Ba^{2+}$ and $Sr^{2+}$, or a mixture of at least two of these divalent cations. The divalent cation, for example $Ca^{2+}$, can be combined with a counterion to form for example solutions of the type $CaCl_2$ or $CaCO_3$, which are well known to the person skilled in the art. The crosslinking solution can also be a solution comprising $CaCO_3$ coupled with glucono delta-lactone (GDL) forming a $CaCO_3$-GDL solution. The crosslinking solution can also be a mixture of $CaCO_3$—$CaSO_4$-GDL. In a particular embodiment of the process according to the invention, the crosslinking aerosol consists of microdroplets of a crosslinking solution comprising calcium, in particular in the form $Ca^{2+}$. The person skilled in the art is able to adjust the nature of the divalent cation and/or counterion, as well as its concentration to the other parameters of the process of the present invention, in particular to the nature of the polymer used and to the desired speed and/or degree of crosslinking. For example, the concentration of the divalent cation in the crosslinking solution is between 10 and 1000 mM. The crosslinking solution may include other constituents, well known to the person skilled in the art, than those described above, in order to improve the crosslinking of the hydrogel sheath under the particular conditions, in particular time and/or temperature.

Advantageously, the crosslinking aerosol is formed of microdroplets of crosslinking solution, the diameter of which is advantageously between 0.5 and 20 µm, preferentially between 1 and 10 µm, more preferentially equal to 5 µm±2 µm.

In an embodiment, the microdroplets of crosslinking solution or the solid microparticles forming the aerosol have a falling velocity lower than the velocity at which the mixed drops are projected by the extrusion flow through the crosslinking aerosol. Preferentially, the microdroplets of crosslinking solution or the solid microparticles forming the aerosol are statically suspended in the air. In an embodiment, the mixed drops fall by gravity through the crosslinking aerosol and the falling velocity of the mixed drops through the crosslinking aerosol is higher than the falling velocity of the crosslinking microdroplets or solid microparticles.

In an embodiment, the aerosol of microdroplets of crosslinking solution has a density of $3*10^3$ microdroplets per $cm^3$.

Advantageously, the aerosol volume of microdroplets of crosslinking solution is maintained in an enclosure, the dimensions of which are adapted to maintain the desired aerosol density and/or concentration. Such containment further enables said aerosol to be kept sterile.

The microdrops of crosslinking solution coalesce, preferably uniformly, on the surface of the mixed drops, so as to promote at least partial crosslinking of the hydrogel layer over the entire surface of said mixed drops. For example, each mixed drop having a diameter of between 50 and 500 µm is surrounded by at least 100 microdroplets of crosslinking solution before reaching the surface for receiving at least partially crosslinked mixed drops in capsules. The skilled person is able to adapt the drop height, the density of the microdroplets in the aerosol and/or the aerosol flow rate so as to obtain a layer of microdroplets around each mixed drop according to their surface. The dropping height is defined as the distance travelled by the mixed drops through the aerosol between the extruder outlet and the receiving surface of said at least partially crosslinked mixed drops in capsules.

In a particular example embodiment, an aerosol of microdroplets of crosslinking solution having a density of $3*10^3$ microdroplets per $cm^3$ is used, said aerosol being sprayed with a flow rate of 20 L/h, within an enclosure of approximately 20 cm in diameter, making it possible to maintain a sufficient density of aerosol by isolating it from the ambient air, while maintaining a height of fall of the mixed drops in the aerosol of 60 cm.

In a particular embodiment, the microdroplets of the crosslinking solution are charged so that they repel each other, thus promoting the electrodispersion of the microdroplets in the aerosol. This can be achieved, for example, by applying direct current to the crosslinking solution before spraying or fogging in an aerosol.

Alternatively or additionally, the mixed drops, and more particularly the layer of hydrogel solution, are charged. In this way, the mixed drops disperse over a larger cross-sectional radius as they pass through the crosslinking aerosol. This reduces the required drop height by increasing the volume of aerosol useful for crosslinking. Indeed, a mixed drop passing on the same trajectory as the previous one encounters fewer crosslinking microdroplets. Moreover, this also reduces the risk of agglomeration/melting of the mixed drops in flight and on impact.

In the case where the microdroplets of crosslinking solution and the mixed drops are charged, the charges are advantageously opposed, so as to favor the deposition of the microdroplets around the surface of the mixed drops.

In an embodiment, the crosslinking aerosol has an osmolarity, or osmotic concentration, 0.1 to 10 times greater than the osmolarity of the composition of interest forming the central core of the capsules. Preferentially, the crosslinking aerosol has an osmolarity, or osmotic concentration, from 0.3 to 3 times greater than the osmolarity of the composition of interest forming the central core of the capsules. In another embodiment, the crosslinking aerosol and the composition of interest forming the central core of the capsules are iso-osmotic, i.e. have substantially equal osmotic concentrations. For example, in the case where the composition of interest is a composition of cells, the crosslinking aerosol is formed from a 100 mM calcium solution. In general, the crosslinking aerosol should not be hyper-osmotic in order to avoid deformation of the mixed drop generated by osmotic pressure and to preserve the structure of the capsules.

According to the invention, it is possible to receive the pre-rigidified capsules after passing through the crosslinking aerosol in a recovery bath. In this case, the recovery bath is preferably iso-osmotic with the composition of interest forming the central core of the capsules.

In an embodiment, the recovery bath may include a crosslinking solution to further crosslink the hydrogel if necessary. Such a crosslinking solution may, if necessary, include a surfactant. Otherwise, in particular in the case where the crosslinking of the hydrogel on falling through the crosslinking aerosol is sufficient, the crosslinking bath may comprise a simple saline solution.

Advantageously, the mixed drops are free of surfactant. In particular, the hydrogel composition is advantageously free of surfactant. Similarly, the capsules according to the invention are advantageously free of surfactants, both in the crosslinked hydrogel layer and in the central core.

Advantageously, the hydrogel solutions and the composition of interest are coextruded so as to form mixed drops, and then capsules, spherical with a diameter between 50 and 500 µm. In a particular embodiment, the thickness of the outer hydrogel shell represents 5 to 40% of the radius of the capsules. In the context of the invention, "thickness" is the dimension extending radially from the center of the capsule. The person skilled in the art knows how to adapt the coextrusion parameters to obtain such dimensions.

According to the invention, the composition of interest means any composition capable of being coextruded with a hydrogel solution to form capsules containing one drop of said composition of interest. Advantageously, the composition of interest is a liquid, aqueous or gelled composition. In an embodiment, the aqueous composition is a gelled aqueous composition. In particular, it is possible to use a composition comprising cells, a food composition, a cosmetic composition or a pharmaceutical composition. For example, the composition of interest is a protein gel and/or a cell gel.

According to the invention, any type of cell composition can be used. In particular, it is possible to make hydrogel capsules surrounding human pluripotent stem cells. A pluripotent stem cell, or pluripotent cell, is defined as a cell that has the capacity to form all tissues present in the entire organism of origin, without being able to form a whole organism as such. In particular, the capsules according to the invention may contain induced pluripotent stem (IPS) cells, for example from somatic cells. More generally, in the context of the invention, the cell compositions do not include cells derived from a human embryo.

In a particular embodiment, the hydrogel solution is an alginate solution (for example SLG100), the composition of interest for forming the central core comprises cells (for example IPS cells resuspended in Matrigel®), and the crosslinking aerosol comprises microdroplets of an aqueous solution of calcium chloride.

EXAMPLE

Example 1

Protocol for Producing Hydrogel Capsules Containing a Composition of Human Pluripotent Cells Solutions Used:
Solution 1, DMEMF12 medium base supplemented with 2 µM Thiazovivin
Solution 2, magnesium and calcium-free PBS supplemented with 1 µM Thiazovivin
Solution 3, non-enzymatic cell detachment buffer: RelesR™ supplemented with 2 µM Thiazovivin.
Solution 4, pluripotent stem cell culture medium: MTeSR1™ hES/hIPS cell medium STEMCELL™).
Solution 4+, Solution 4 supplemented with 2 µM Thiazovivin.
Solution 5, Matrigel™.
Solution 6, 300 mM sorbitol with 2 µM Thiazovivin.
Cell Solution:
A 25 cm² Petri dish of human IPS cells at 90% confluence is then used to match the recommended volumes. All subsequent steps are performed at 4° C. to the extruder exit.
Step 1: Rinse the cells with solution 1. Wait 10 minutes to 1 hour.
Step 2: Rinse twice with 4 mL of Solution 2.
Step 3: Gently aspirate the solution.
Step 4: Incubate the cells with 4 mL of solution 3 for 5-10 minutes.
Step 5: Detach the cells with 2 mL of solution 4+ with a wide tip pipette to reduce shear stress.
Step 6: Centrifuge the cell suspension at 360 g for 5 minutes.
Step 7: Aspirate the supernatant.
Step 8: Resuspend with 0.5 mL of solution 4+.
Step 9: Centrifuge again at 360 rcf and aspirate the supernatant.
Step 10: Resuspend the cell pellet in 70 µL of solution 5 and 100 µL of solution 6 (pellet volume should be 30 µL). The cell solution is ready.
Encapsulation:
The encapsulation device (extruder) is prepared as described in Alessandri et al., 2016 ("A 3D printed microfluidic device for production of functionalized hydrogel microcapsules for culture and differentiation of human Neuronal Stem Cells (hNSC)", Lab on a Chip, 2016, vol. 16, no. 9, p. 1593-1604), with two modifications: the absence of surfactant in the alginate solution and the presence of a 50 cm high enclosure around the formation bath to contain an aerosol from the nebulization of the same solution as that of the crosslinking bath (300 mosmol $CaCl_2$).
In summary, the different parts of the device are sterilized (by autoclave); the three necessary solutions are loaded on three syringe barrels, i) alginate solution (PRONOVA®SLG100 at 2% by mass in distilled water), ii) intermediate solution (300 mM sorbitol), iii) cell solution (prepared in the previous step); The three solutions are co-injected in a concentric manner using a microfluidic injector which allows the formation of a jet which splits into drops, the outer layer of which is the alginate solution and the core the cell solution;

To electrodisperse the drops, the alginate was charged with a direct current at +2 kV. A 2 cm diameter ground ring is placed 2 mm from the tip in the plane perpendicular to the axis of the jet exiting the microfluidic injector to generate the electric field.

After splitting of the jet and electrodispersion of the drops, they pass through the aerosol of crosslinking solution contained in the enclosure (of the order of about $3*10^E9$ droplets per cubic meter of gas, each droplet has a diameter of 1 to 10 µm and contains a 100 mM aqueous calcium solution). The coalescence of droplets of crosslinking solution on the surface of the mixed droplets rigidifies their surface and allows them to penetrate into the calcium bath (recovery/crosslinking bath) while maintaining their internal structure. These drops are collected in a calcium bath (at 100 mM) which finalizes the crosslinking of the alginate solution to form the shell.

Note that under these encapsulation conditions, the crosslinking of the alginate layer occurs spontaneously.

Treatment after Encapsulation:
Step 1: The capsules are collected with a 40 µm cell sieve and after rinsing with solution 1 they are stored in a 75 cm² flask with 20 mL of solution 4+.
Step 2: The flask is kept for 12 h in the incubator at 37° C. and 5% $CO^2$.
Step 3: Change the medium for solution 4 to allow cysts to form.
Step 4: After 24 to 72 h cysts of a few dozen cells form in the capsules. The cell microcompartments are mature after 5 to 10 days.

The invention claimed is:
1. A process for the manufacture of a plurality of capsules each comprising a crosslinked hydrogel outer shell surrounding a central core, wherein a hydrogel solution and a composition of interest comprising cells, designed to form the central core, are concentrically coextruded to form mixed drops each comprising a layer of the hydrogel solution surrounding a drop of the composition of interest comprising cells, the coextrusion step being carried out above a crosslinking aerosol so that the mixed drops pass through said crosslinking aerosol, so that the layer of the hydrogel solution at least partially crosslinks around the drop of the composition of interest comprising cells in contact with said aerosol, said capsules being spherical and having a diameter comprised between 50 and 500 µm, characterized in that the composition of interest comprising cells is an aqueous composition of interest and the osmotic concentration of the crosslinking aerosol is comprised between 0.3 to 3 times the osmotic concentration of the composition of interest comprising cells and forming the central core of the capsules; wherein the mixed drops are free of a surfactant.

2. The process as claimed in claim 1, wherein the crosslinking aerosol is formed from microdroplets of crosslinking solution, the diameter of which is comprised between 0.5 and 20 µm.

3. The process as claimed in claim 2, wherein the microdroplets of crosslinking solution forming the aerosol have a falling velocity lower than the velocity at which the mixed drops are projected by the extrusion flow through the crosslinking aerosol.

4. The process as claimed in claim 1, wherein the capsules are immersed in a recovery bath after passing through the crosslinking aerosol, said recovery bath comprising a crosslinking solution.

5. The process as claimed in claim 1, wherein the crosslinking aerosol and the composition of interest forming the central core of the capsules are iso-osmotic.

6. The process as claimed in claim 1, wherein the mixed drops are charged so as to disperse and the crosslinking aerosol is oppositely charged or neutral.

7. The process as claimed in claim 1, wherein the composition of interest designed to form the central core is selected from a cell solution, a food composition, a cosmetic composition or a pharmaceutical composition.

8. The process as claimed in claim 1, wherein the hydrogel solution is an alginate solution, the composition of interest designed to form the central core comprises cells and the crosslinking aerosol comprises microdroplets of a calcium chloride solution.

9. The process of claim 2, wherein the crosslinking aerosol is formed from microdroplets of crosslinking solution, the diameter of which is between 1 and 10 μm.

10. The process of claim 9, wherein the crosslinking aerosol is formed from microdroplets of crosslinking solution, the diameter of which is equal to 5 μm±2 μm.

* * * * *